(12) United States Patent
Chen

(10) Patent No.: US 12,303,208 B2
(45) Date of Patent: May 20, 2025

(54) METHOD AND SYSTEM TO AUGMENT MEDICAL SCAN IMAGE INFORMATION ON EXTENDED REALITY IMAGE

(71) Applicant: BRAIN NAVI BIOTECHNOLOGY CO., LTD, Zhubei (TW)

(72) Inventor: Chieh Hsiao Chen, Santa Clara, CA (US)

(73) Assignee: BRAIN NAVI BIOTECHNOLOGY CO., LTD, Zhubei (TW)

( * ) Notice: Subject to any disclaimer, the term of this patent is extended or adjusted under 35 U.S.C. 154(b) by 295 days.

(21) Appl. No.: 17/919,989

(22) PCT Filed: Apr. 21, 2021

(86) PCT No.: PCT/CN2021/088799
§ 371 (c)(1),
(2) Date: Oct. 19, 2022

(87) PCT Pub. No.: WO2021/213450
PCT Pub. Date: Oct. 28, 2021

(65) Prior Publication Data
US 2023/0149087 A1    May 18, 2023

Related U.S. Application Data

(60) Provisional application No. 63/013,687, filed on Apr. 22, 2020.

(51) Int. Cl.
*A61B 34/10* (2016.01)
*A61B 90/00* (2016.01)
(Continued)

(52) U.S. Cl.
CPC .............. *A61B 34/10* (2016.02); *A61B 90/37* (2016.02); *G06T 19/006* (2013.01); *G06T 19/20* (2013.01);
(Continued)

(58) Field of Classification Search
None
See application file for complete search history.

(56) References Cited

U.S. PATENT DOCUMENTS 9,547,940 B1 *   1/2017  Sun .......................... G06T 7/344
2008/0049999 A1  2/2008  Jerebko et al.
(Continued)

OTHER PUBLICATIONS

International Search Report and the Written Opinion of the International Searching Authority for PCT Application No. PCT/CN2021/088799, dated Jul. 21, 2021.

*Primary Examiner* — James A Thompson
(74) *Attorney, Agent, or Firm* — Haverstock & Owens, A Law Corporation

(57) ABSTRACT

Embodiments of the present disclosure set forth a method to augment medical scan information associated with a target object on a first extended reality image. The method includes obtaining a three-dimensional image associated with the target object, identifying a first set of three-dimensional feature points from the three-dimensional image, identifying anatomical points based on the first set of three-dimensional feature points, obtaining the first extended reality image associated with the anatomical points; selecting a second set of three-dimensional feature points from the first extended reality image, performing a first image matching between the first set of three-dimensional feature points and the second set of three-dimensional feature points, and superimposing the three-dimensional image on the first extended reality image based on the first image matching.

12 Claims, 7 Drawing Sheets

(51) Int. Cl.
*G06T 19/00* (2011.01)
*G06T 19/20* (2011.01)
*G06V 20/64* (2022.01)
*G16H 30/40* (2018.01)

(52) U.S. Cl.
CPC ........... *G06V 20/653* (2022.01); *G16H 30/40* (2018.01); *A61B 2034/105* (2016.02); *A61B 2034/107* (2016.02); *A61B 2090/365* (2016.02); *G06T 2200/04* (2013.01); *G06T 2210/41* (2013.01); *G06T 2219/2016* (2013.01); *G06V 2201/03* (2022.01)

(56) References Cited

U.S. PATENT DOCUMENTS

| | | |
|---|---|---|
| 2013/0310690 A1 | 11/2013 | Chang et al. |
| 2015/0049174 A1 | 2/2015 | Lee et al. |
| 2017/0367771 A1* | 12/2017 | Tako ...................... G16H 20/40 |
| 2018/0092698 A1* | 4/2018 | Chopra .................. A61B 90/39 |
| 2019/0188461 A1 | 6/2019 | Wang et al. |
| 2019/0392265 A1 | 12/2019 | Spottiswoode et al. |
| 2021/0279949 A1* | 9/2021 | Cao ......................... G06T 17/00 |

\* cited by examiner

METHOD AND SYSTEM TO AUGMENT MEDICAL SCAN IMAGE INFORMATION ON EXTENDED REALITY IMAGE

CROSS-REFERENCE TO RELATED APPLICATION

This application claims the benefit of U.S. Provisional Application No. 63/013,687 filed Apr. 22, 2020, which is incorporated by reference in its entirety.

BACKGROUND OF THE INVENTION

Field of the Invention

Embodiments of the present invention relate generally to methods and systems to augment medical scan image information on an extended reality image.

Description of the Related Art

Unless otherwise indicated herein, the approaches described in this section are not prior art to the claims in this application and are not admitted to be prior art by inclusion in this section.

In an operation, a plan of an operation pathway is critical. The operation pathway may be defined by multiple points, such as a safety point and a preoperative point away from the patient, an entry point on patient's tissues, and a target point at the target of the operation.

Before the operation, the patient is subjected to a medical scan (e.g., CT or MRI). The medical scan may provide images of tissues, organs and organ systems of the patient. The operation pathway is planned based on the medical scan images. For example, artificial intelligence may be employed to suggest a surgeon with best routes that incur the least amount of damages.

Extended reality technology generally refers a technology including one or more real-and-virtual combined environment and one or more human-machine interfaces generated by computer technologies and one or more wearables. Extended reality, including virtual reality, augmented reality and mixed reality, is increasingly used in medical fields. For example, extended reality may display virtual images of tissues, organs and organ systems adjacent to the operation pathway and augment medical scan information (e.g., medical scan images) on the virtual images to facilitate the operation.

However, there is a non-trivial difference in time between when the medical scan is performed on a patient and when the operation is performed. Conventional extended reality technology does not adequately reconcile the differences with respect to virtual images adjacent to the operation pathway and information obtained in the medical scan.

DETAILED DESCRIPTION

Figure 1:
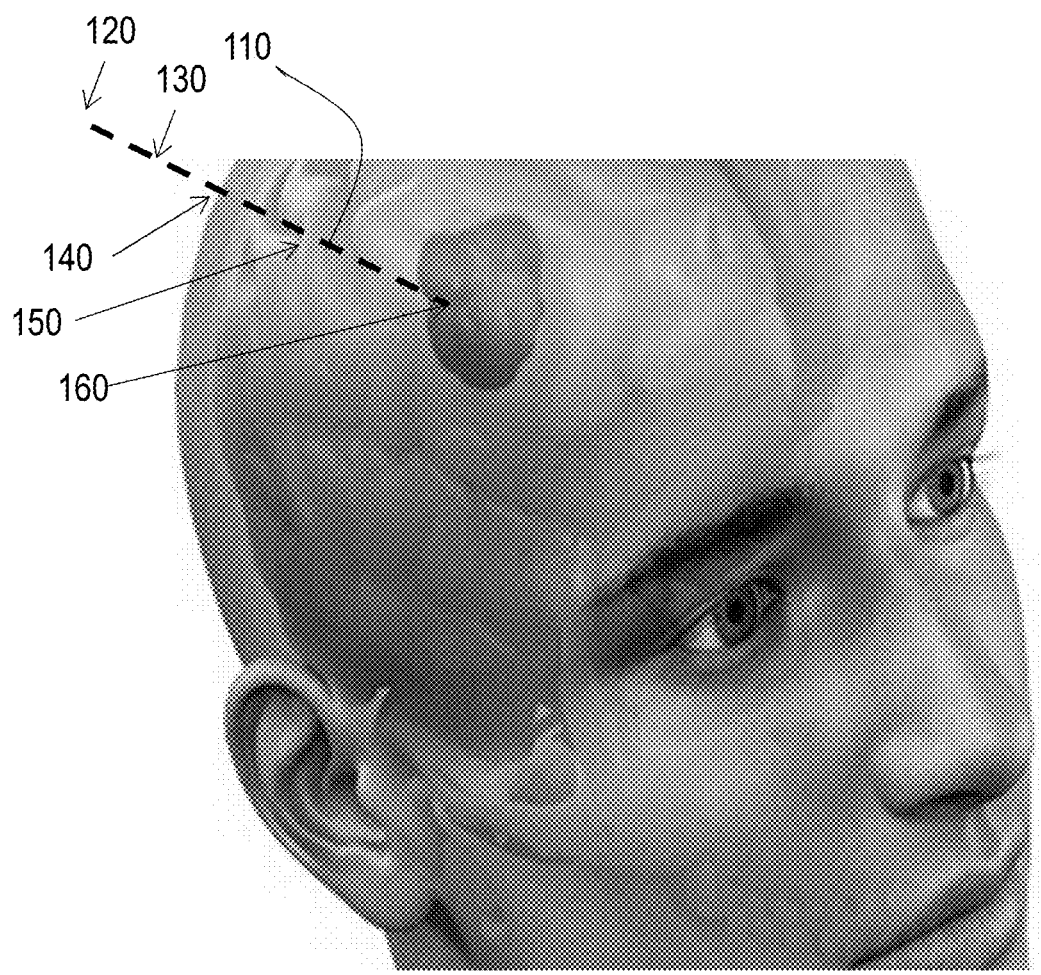
FIG. 1 is an example figure showing the spatial relationships among several points that may be encountered when performing an operation on a patient.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

Throughout the following paragraphs, "extended reality (XR)" generally refers to an environment that combines virtual and physical realities, where the 'X' represents a variable for any current or future spatial computing technologies. In some embodiments, extended reality is an umbrella term for all environments that combine virtual and physical realities. For example, extended reality includes augmented, virtual, and mixed realities. An "extended reality image" broadly refers to an image containing information in both virtual and physical realities. "Wearable," "wearable technology," and "wearable device" are used interchangeably to generally refer to hands-free devices that can be worn on a person as accessories, embedded in clothing, implanted in a person's body, etc. Such devices typically can detect, collect, analyze, and/or communicate information associated with the wearer, such as vital signs, movement data, and/or ambient data. Examples of a wearable may include, without limitation, a headset, smart glasses, etc. A three-dimensional (3D) model broadly refers to a collection of points in 3D space, connected by various geometric entities such as triangles, lines, curved surfaces, etc.

FIG. 1 is an example figure showing spatial relationships among several points that may be encountered when performing an operation on a patient, arranged in accordance with some embodiments of the present disclosure. In FIG. 1, an operation pathway 110 may include safety point 120, preoperative point 130, entry point 140, transient point 150 and target point 160. Safety point 120 may be a point for a robotic arm to perform an operation to move or rotate without causing any injury to the patient. Preoperative point 130 may be a point corresponding to a position and an angle of the robotic arm configured to perform the operation but not yet in physical contact with the patient. Entry point 140 may be a point that the robotic arm is in contact with the patient for the first time along the operation pathway 110. Target point 160 may be a point associated with a target tissue or a target organ of the operation. Transient point 150 may be a point between entry point 140 and target point 160.

Figure 2:
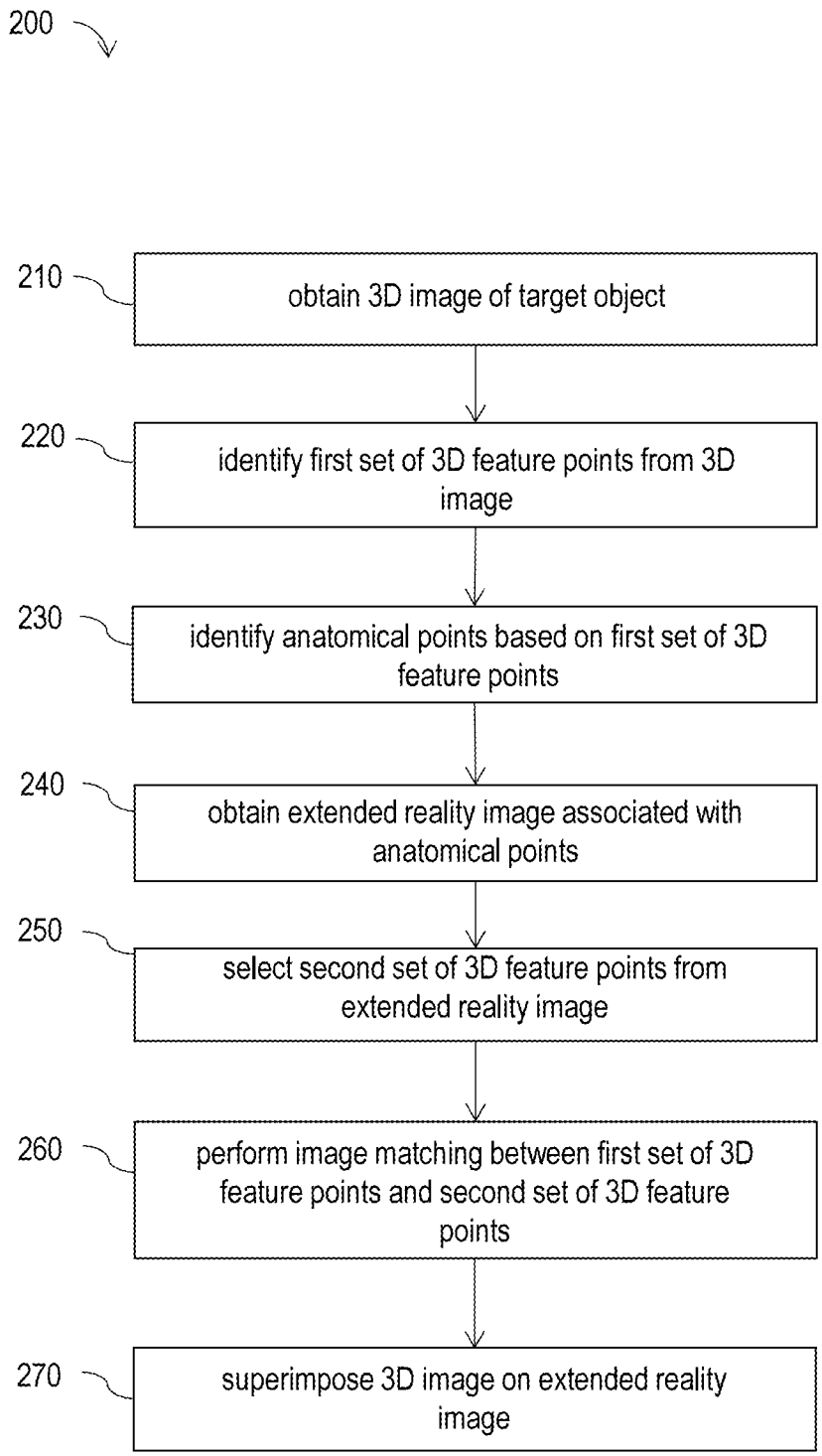
FIG. 2 is a flow diagram illustrating an example process to associate a three-dimensional image of a target object with an extended reality image of the target object.

FIG. 2 is a flow diagram illustrating an example process 200 to associate a three-dimensional image of a target object with an extended reality image of the target object, arranged in accordance with some embodiments of the present disclosure. Process 200 may include one or more operations, functions, or actions as illustrated by blocks 210, 220, 230, 240, 250, 260, and/or 270 which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 200 may begin at block 210, "obtain three-dimensional (3D) image of target object." In some embodiments, for illustrations only, the target object may be a part of a tissue, an organ, an organ system of a patient. One of the three-dimensional images may correspond to an image taken by a three-dimensional camera (e.g., a camera with a depth sensor) or a set of images taken by two-dimensional cameras. Another of the three-dimensional images may also correspond an image obtained by another source, such as a medical scan device (e.g., an ultrasound scanner, a computerized tomography (CT) scanner, a magnetic resonance imaging (MRI) device, etc.). In some embodiments, any of the three-dimensional images may correspond to surface anatomy information of a tissue, an organ, an organ system of the patient. In some embodiments, the camera(s) may be configured to take images of the patient's head to capture the head appearance and contours (e.g., eyes, ears, nose tip, nostril opening, earlobe, etc.) of the patient. The three-dimensional camera or the two-dimensional cameras may be coupled to a wearable device of a surgeon who performs the operation on the patient. Alternatively, the three-dimensional camera or the two-dimensional cameras may be coupled to an endoscope or a surgical tool controlled by a robotic arm.

It should be noted that these 3D images are considered to include physical reality information captured by devices in the physical reality (e.g., 3D camera, 2D camera, medical scan device, etc.)

Block 210 may be followed by block 220 "identify first set of 3D feature points from 3D image." In some embodiments, an artificial intelligence engine may be employed to identify a first set of 3D feature points from the 3D image obtained in block 210. The artificial intelligence engine may be based on edges, contrasts, shapes to identify the first set of 3D feature points. In some alternative embodiments, the first set of 3D feature points may be identified by a surgeon through a wearable device.

Block 220 may be followed by block 230 "identify anatomical points based on first set of 3D feature points." In some embodiments, the first set of 3D feature points are shown or marked on the 3D image obtained in block 210 to identify anatomical points of the patient corresponding to the first set of 3D feature points. For example, by showing or marking the first set of 3D feature points on a 3D facial image of the patient, anatomical points (e.g., eyes, ears, nose tip, nostril opening and earlobe) of the patient corresponding to the first set of 3D feature points may be identified. Alternatively, by showing or marking the first set of 3D feature points on a 3D endoscopic image of the patient, anatomical points (e.g., vessels of an organ) of the patient corresponding to the first set of 3D feature points may be identified. In block 230, one or more tissues, one or more organs and one or more organ systems of the patient include the anatomical points may also be identified.

Block 230 may be followed by block 240 "obtain extended reality image associated with anatomical points." In some embodiments, based on identified one or more tissues, one or more organs, or one or more organ systems of the patient including the anatomical points, an extended reality image associated with the one or more tissues, one or more organs, or one or more organ systems of the patient may be obtained. For example, this extended reality image may be an XR image of a surface of the patient's head that is to be displayed in a wearable device (e.g., a headset, smart glasses, etc.). In alternative embodiments, this extended reality image may be an XR image of a surface of an organ (e.g., liver or brain) of the patient that is to be displayed in the wearable device. These XR images include information captured in the physical reality (e.g., one or more images of the patient's head, one or more images of the patient's organ, etc.) and also the rendered image in the virtual reality.

Block 240 may be followed by block 250 "select second set of 3D feature points from extended reality image." In some embodiments, based on the identified anatomical points, a second set of 3D feature points are selected from the extended reality image obtained in block 240. The second set of 3D feature points may correspond to the identified anatomical points.

Block 250 may be followed by block 260 "perform image matching between first set of 3D feature points and second set of 3D feature points." In some embodiments, the first set of 3D feature points and the second set of 3D feature points are matched to determine a relationship that aligns the first set of 3D feature points and the second set of 3D feature points, sometimes iteratively to minimize the differences between the two sets of 3D feature points. The image matching may be based on some image comparison approaches, such as iterative closest point (ICP). Based on the determined relationship that aligns the first set of 3D feature points and the second set of 3D feature points, the three-dimensional image of the target object is associated with the extended reality image of the target object. In some embodiments, for example in a Cartesian coordinate system, the determined relationship may include, but not limited to, a first shift along the X-axis, a second shift along the Y-axis, a third shift along the Z-axis, a first rotation angle along the X-axis, a second rotation angle along the Y-axis and a third rotation angle along the Z-axis. The determined relationship may be different in various coordinate systems.

Block 260 may be followed by block 270 "superimpose 3D image on extended reality image." In some embodiments, based on the relationship determined in block 260 that aligns the first set of 3D feature points and the second set of 3D feature points, the three-dimensional image of the target object is associated with the extended reality image of the target object. Accordingly, the three-dimensional image of the target object obtained in block 210 may be superimposed on the extended reality image associated with anatomical points obtained in block 240 to augment additional information obtained in block 210 on the extended reality image obtained in block 240.

Figure 3:
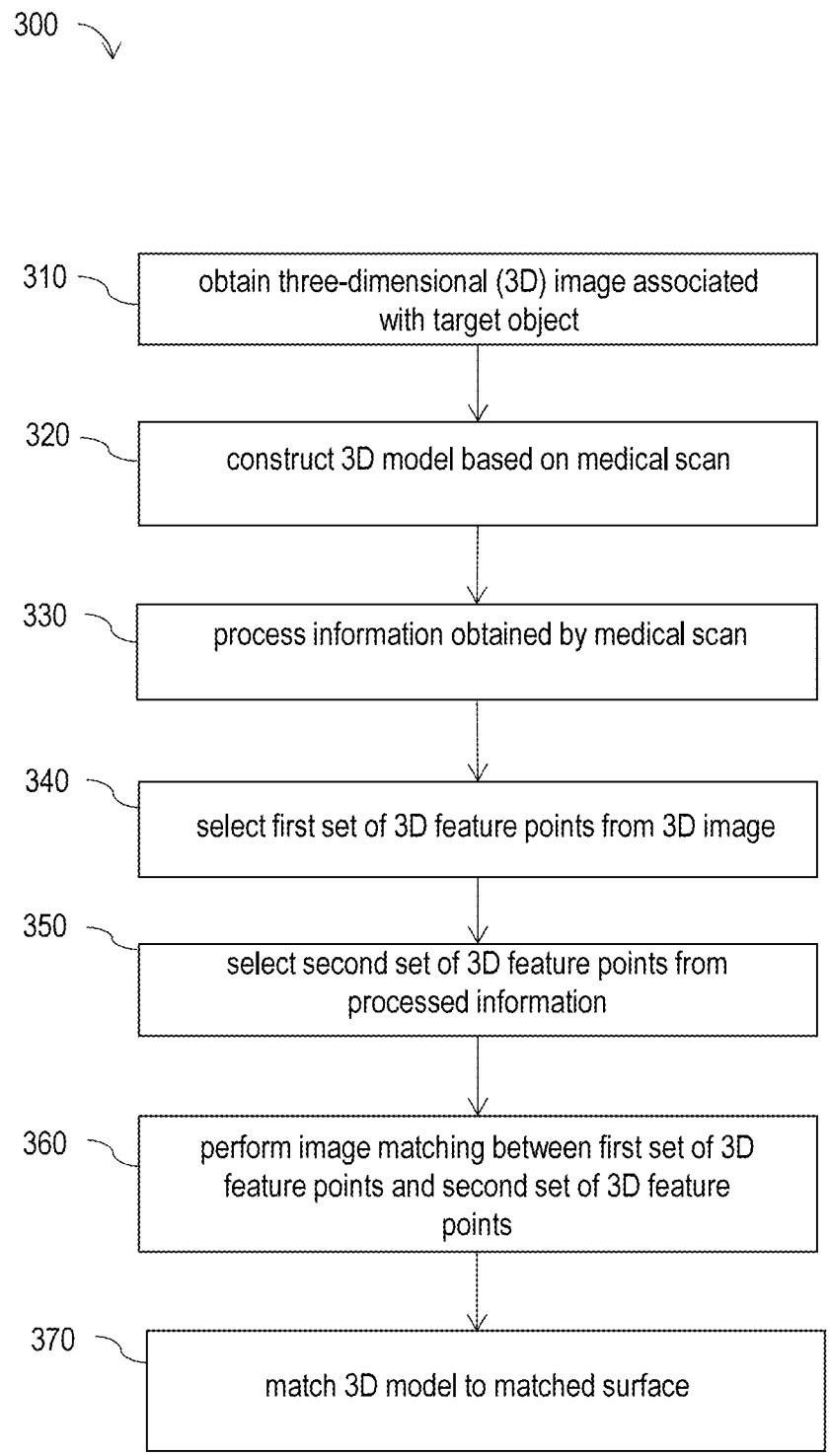
FIG. 3 is a flow diagram illustrating an example process to associate a three-dimensional image of a target object with a medical scan image including the target object.

FIG. 3 is a flow diagram illustrating an example process 300 to associate a three-dimensional image of a target object with a medical scan image including the target object, arranged in accordance with some embodiments of the present disclosure. Process 300 may include one or more operations, functions, or actions as illustrated by blocks 310, 320, 330, 340, 350, 360 and/or 370 which may be performed by hardware, software and/or firmware. In some embodiments, in conjunction with FIG. 1, process 300 may be performed in response to that a surgical tool reaches entry point 140. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 300 may begin at block 310, "obtain three-dimensional (3D) image associated with target object." In some embodiments, for illustrations only, the target object may be a part of a tissue, an organ, an organ system of a patient. The three-dimensional image may include an image taken by a three-dimensional camera (e.g., a camera with a depth sensor) or a set of images taken by two-dimensional cameras. In some embodiments, the three-dimensional image may correspond to surface anatomy information of a tissue, an organ, an organ system of the patient. In some embodiments, the camera(s) may be configured to take images of the patient's head to capture the head appearance and contours (e.g., eyes, ears, nose tip, nostril opening, earlobe, etc.) of the patient. The three-dimensional camera or the two-dimensional cameras may be fixed at a wearable of a surgeon who performs an operation to the patient. Alternatively, the three-dimensional camera or the two-dimensional cameras may be fixed at an endoscope or a surgical tool controlled by a robotic arm.

Block 310 may be followed by block 320, "construct 3D model based on medical scan." Before an operation is performed, some medical scans may be used to capture a snapshot of a patient's conditions, so that an operation plan may be formulated. The operation plan may include a planned operation pathway as set forth above. For example, the surgeon may order a medical scan (e.g., CT or MRI) to obtain medical scan images including a target object (e.g., one or more tissues or organs of a patient). Such a medical scan may be performed a few days (e.g., 3 to 5 days) prior to the operation. A three-dimensional model associated with the target object may be constructed based on information of images obtained from the medical scan data using some known approaches.

Figure 4A:
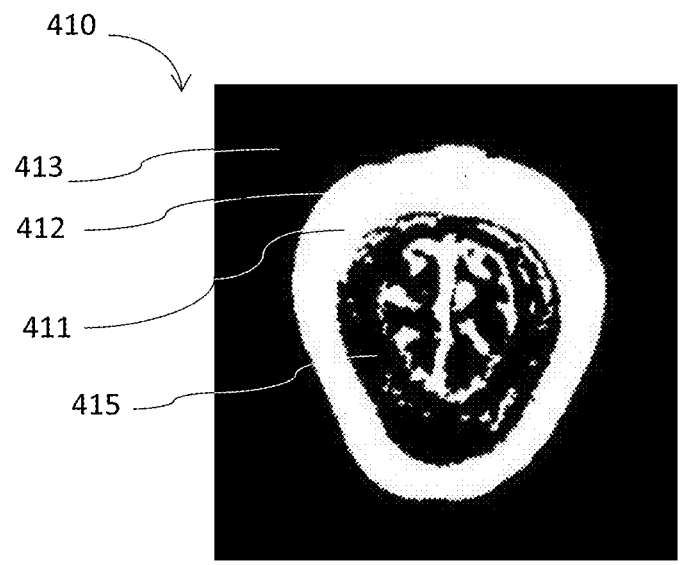
FIGS. 4A and 4B illustrate example processed images based on a medical scan image.
Figure 4A:
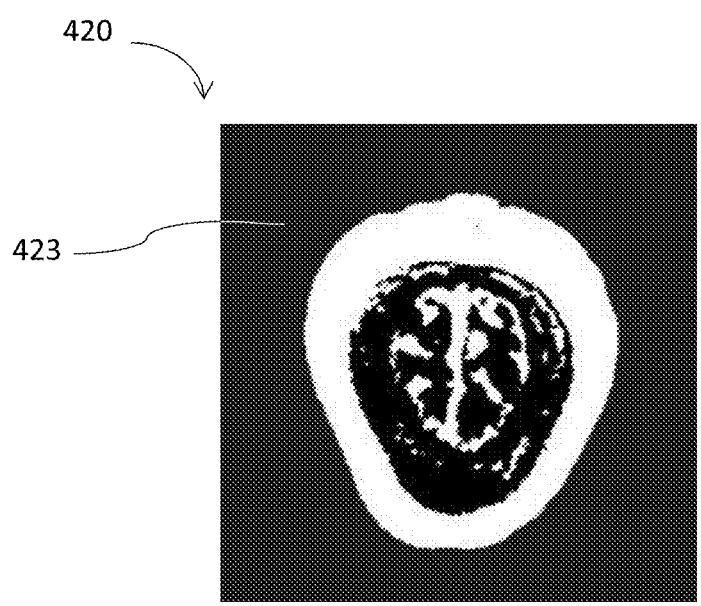
Figure 4B:
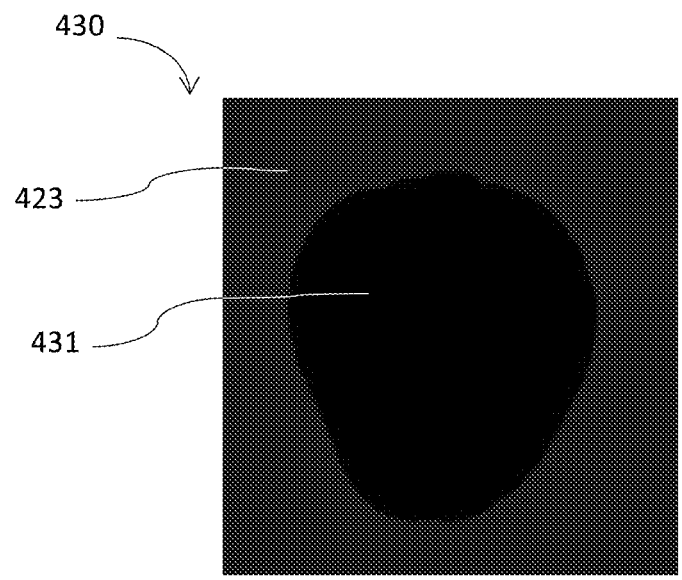
Figure 4B:
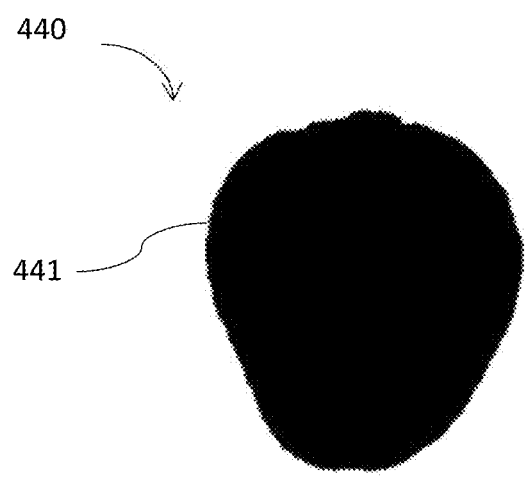

FIGS. 4A and 4B illustrate processed images based on a medical scan image, arranged in accordance with some embodiments of the present disclosure. In conjunction with FIGS. 4A and 4B, block 320 may be followed by block 330, "process information obtained by medical scan," in accordance with some embodiments of the present disclosure. The 3D images obtained in block 310 are only associated with a surface information of the target object but are not associated with the under-surface information of the target object. However, images obtained by medical scans usually are associated with both the surface and the under-surface information. Image processing is performed to remove the under-surface information from the medical scans.

In FIG. 4A, in some embodiments, assuming an operation target is inside the patient's head, binary image 410 may be derived from an original MRI image along an axial direction from head to toes of the patient. Region 411 is the skull of the patient and is usually represented in white in the original MRI image. The outer periphery 412 of region 411 may refer to the patient's skin, which is associated with the surface information of the target object (i.e., patient's head). With thresholding approach, image 410 including region 413 outside of the skull (all black) and region 415 inside the skull may be created. Image 410 may be further processed to form image 420. In image 420, region 413 is assigned a gray scale to be differentiated from black and white to form region 423.

In FIG. 4B, image 420 may be further processed to form image 430. In image 430, regions other than the gray scale of region 413 are assigned with black to form region 431. Region 423 in image 430 may then be assigned with white to form image 440. Therefore, points along periphery 441 may correspond to the patient's skin, which is associated with the surface information of the target object. Accordingly, points along periphery 441 do not include the under-surface information obtained by the medical scans.

Block 330 may be followed by block 340 "select first set of 3D feature points from 3D image." In some embodiments, an artificial intelligence engine may be employed to select a first set of 3D feature points from the 3D image obtained in block 310. The artificial intelligence engine may be based on edges, contrasts, shapes to select the first set of 3D feature points. In some embodiments, the first set of 3D feature points may correspond to anatomical feature points, such as vessel distributions or tissue textures of an organ.

Block 340 may be followed by block 350 "select second set of 3D feature points from processed information." In some embodiments, an artificial intelligence engine may be employed to select a second set of 3D feature points from information obtained by medical scan processed in block 330. The artificial intelligence engine may be based on edges, contrasts, shapes to select the second set of 3D feature points. In some embodiments, the second set of 3D feature points may correspond to same anatomical feature points corresponding to the first set of 3D feature points selected in block 340.

Block 350 may be followed by block 360 "perform image matching between first set of 3D feature points and second set of 3D feature points." In some embodiments, the first set of 3D feature points and the second set of 3D feature points are matched to determine a relationship that aligns the first set of 3D feature points and the second set of 3D feature points, sometimes iteratively to minimize the differences between the two sets of 3D feature points. The image matching may be based on some image comparison approaches, such as iterative closest point (ICP). Based on the determined relationship that aligns the first set of 3D feature points and the second set of 3D feature points, the three-dimensional image associated with the target object is associated with the processed image (e.g., image 440) of the target object. In some embodiments, for example in a Cartesian coordinate system, the determined relationship may include, but not limited to, a first shift along the X-axis, a second shift along the Y-axis, a third shift along the Z-axis, a first rotation angle along the X-axis, a second rotation angle along the Y-axis and a third rotation angle along the Z-axis. The determined relationship may be different in various coordinate systems.

Block 360 may be followed by block 370 "match 3D model to matched surface." In some embodiments, based on the relationship determined in block 360 that aligns the first set of 3D feature points and the second set of 3D feature points, a first surface associated with the target object obtained in block 310 and a second surface associated with the 3D model constructed in block 320 based on the medical scans are matched. Several points of the 3D model may define the second surface. Therefore, based on the determined relationship as set forth above, the 3D model constructed in block 320 may be rotated and/or shifted to match one surface defined by several points of the 3D model to the second surface.

Figure 5:
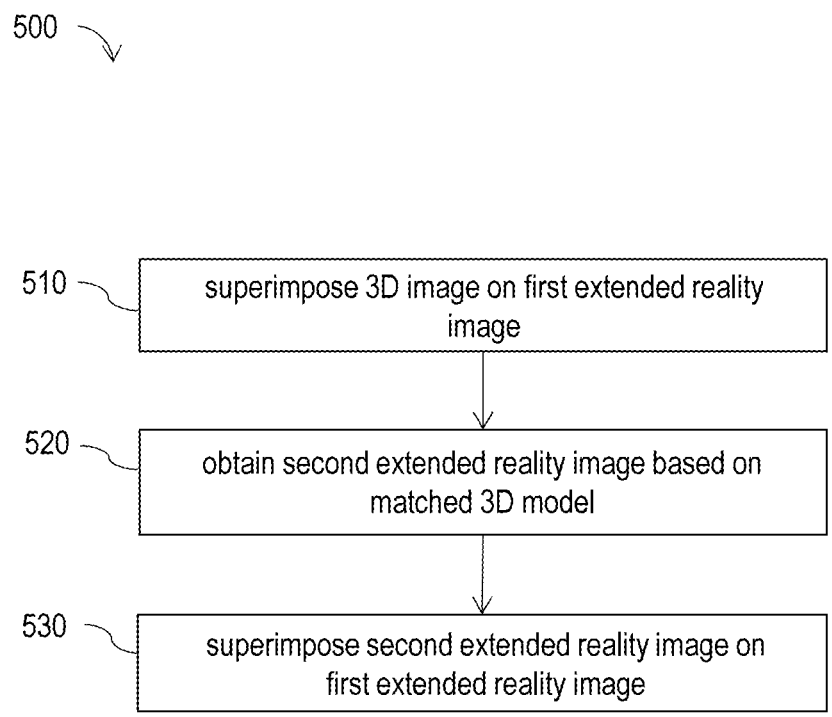
FIG. 5 is a flow diagram illustrating an example process to augment information obtained by a medical scan associated with a target object on an extended reality image of the target object.

FIG. 5 is a flow diagram illustrating an example process to augment information obtained by a medical scan associated with a target object on an extended reality image of the target object, arranged in accordance with some embodiments of the present disclosure. Process 500 may include one or more operations, functions, or actions as illustrated by blocks 510, 520 and/or 530 which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 500 may begin at block 510, "superimpose three-dimensional (3D) image on first extended reality image." In some embodiments, in conjunction with FIG. 2, block 510 may correspond to block 270. For example, in block 510, a three-dimensional image of a target object obtained in block 210 may be superimposed on a first extended reality image associated with anatomical points obtained in block 240 to augment additional information obtained in block 210 on the first extended reality image obtained in block 240.

Block 510 may be followed by block 520, "obtain second extended reality image based on matched 3D model." In some embodiments, in conjunction with FIG. 3, block 370 may be followed by block 520. For example, in block 520, this second extended reality image may be obtained based on the 3D model matched in block 370. This second extended reality image may include one or more surface and under-surface (e.g., tissues or organs) XR images of the patient's head that are to be displayed in a wearable device (e.g., a headset, smart glasses, etc.). In alternative embodiments, this second extended reality image may include one or more surface and under-surface XR images of a tissue (e.g., blood vessel) or an organ (e.g., liver or brain) of the patient that are to be displayed in the wearable device. These XR images include information captured in the physical reality (e.g., medical scan images of the patient) and also the rendered image in the virtual reality.

Block 520 may be followed by block 530, "superimpose second extended reality image on first extended reality image." In some embodiments, because the second extended reality image is obtained based on the 3D model matched in block 370, one surface image of the second extended reality image will be matched to the first surface associated with the target object obtained in block 310, which is also a part of three-dimensional image of the target object obtained in block 210. After identifying the first surface from the three-dimensional image of the target object obtained in block 210, the second extended reality image may be superimposed on the first extended reality image based on the first surface. Because the second extended reality image is obtained from 3D model in block 370 which is also constructed based on the medical scans in block 320, as discussed above, information obtained by the medical scans, including under-surface information, may be augmented on the first extended reality image of the target object.

Figure 6:
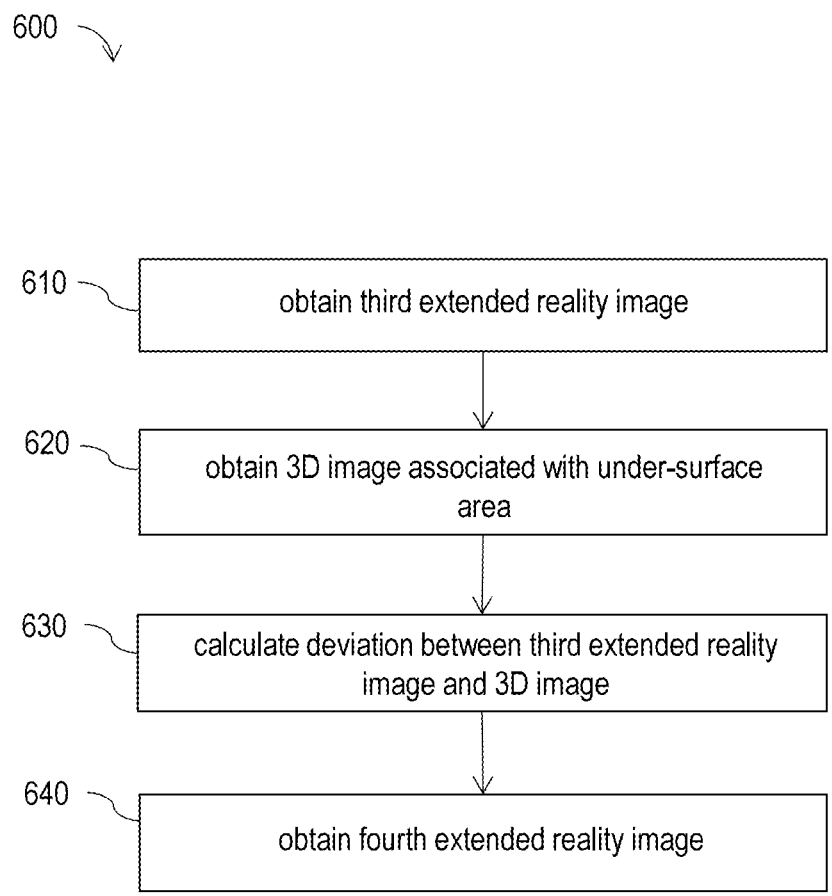
FIG. 6 is a flow diagram illustrating an example process to obtain an extended reality image associated with a target object in response to a shift of the target object when a surgical tool reaches an under-surface area of the target object, all arranged in accordance with some embodiments of the present disclosure.

FIG. 6 is a flow diagram illustrating an example process to obtain an extended reality image associated with a target object in response to a shift of the target object when a surgical tool reaches an under-surface area of the target object, arranged in accordance with some embodiments of the present disclosure. Process 600 may include one or more operations, functions, or actions as illustrated by blocks 610, 620, 630 and/or 640 which may be performed by hardware, software and/or firmware. In some embodiments, in conjunction with FIG. 1, process 600 may be performed in response to that a surgical tool passes entry point 140 and reaches transient point 150. In some embodiments, in conjunction with FIG. 5, process 600 may be performed after block 530. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 600 may begin at block 610, "obtain third extended reality image." In some embodiments, the third extended reality image may correspond to an image associated with an under-surface area (e.g., transient point 150 in FIG. 1) of a target object to simulate a field of view when the surgical tool reaches the under-surface area of the target object. The surgical tool may be attached to a robotic arm in an operation room which has known spatial relationships with the patient. In some embodiments, in conjunction with FIG. 5, after block 530, the second extended reality image has been superimposed on the first extended reality image. Accordingly, in block 610, the third extended reality image may be obtained based on the second extended reality image and the known spatial relationships.

Block 610 may be followed by block 620, "obtain three-dimensional (3D) image associated with under-surface area." In some embodiments, a 3D image associated with the under-surface area may be obtained by a camera or an ultrasound sensor attached on the surgical tool when the surgical tool physically reaches the under-surface area.

Block 620 may be followed by block 630, "calculate deviation between third extended reality image and 3D image." In some embodiments, a deviation between the third extended reality image obtained in block 610 and the three-dimensional image obtained in block 620 is calculated by any technical feasible approaches. The deviation may be cause by the intrusion of the surgical tool. For example, brains include very soft tissues. These tissues are easily shifted from their original locations in response to an intrusion of a foreign object (e.g., the surgical tool).

Block 630 may be followed by block 640 "obtain fourth extended reality image." In some embodiments, the third extended reality image obtained in block 610 may be updated by compensating the deviation calculated in block 630 to obtain a fourth extended reality image. Therefore, the fourth extended reality image may correspond to an image associated with the under-surface area to simulate a field of view when the surgical tool physically reaches the under-surface area of the target object. Accordingly, the fourth extended reality image may include information obtained by the medical scans and can facilitate the surgeon to perform the operation in response to shifts associated with one or more tissues or one or more organs.

In some embodiments, methods 200, 300, 500 and 600 may be performed by a computer connected to a wearable (e.g., Microsoft® HoloLens) in a wired or wireless manner. The computer may provide an extended reality platform which provides reality experiences (e.g., images) on the wearable. The wearable is configured to display extended reality images as set forth above in FIGS. 2, 3, 5 and 6.

The above examples can be implemented by hardware (including hardware logic circuitry), software or firmware or a combination thereof. The above examples may be implemented by any suitable computing device, computer system, wearables, etc. The computing device may include processor(s), memory unit(s) and physical NIC(s) that may communicate with each other via a communication bus, etc. The computing device may include a non-transitory computer-readable medium having stored thereon instructions or program code that, in response to execution by the processor, cause the processor to perform processes described herein with reference to FIGS. 2, 3, 5, and 6. For example, a computing device may communicate with a wearable and/or one or more sensors.

The techniques introduced above can be implemented in special-purpose hardwired circuitry, in software and/or firmware in conjunction with programmable circuitry, or in a combination thereof. Special-purpose hardwired circuitry may be in the form of, for example, one or more application-specific integrated circuits (ASICs), programmable logic devices (PLDs), field-programmable gate arrays (FPGAs), and others. The term 'processor' is to be interpreted broadly to include a processing unit, ASIC, logic unit, or programmable gate array etc.

Some aspects of the embodiments disclosed herein, in whole or in part, can be equivalently implemented in integrated circuits, as one or more computer programs running on one or more computers (e.g., as one or more programs running on one or more computing systems), as one or more programs running on one or more processors (e.g., as one or more programs running on one or more microprocessors), as firmware, or as virtually any combination thereof, and that designing the circuitry and/or writing the code for the software and or firmware are possible in light of this disclosure.

Software and/or other instructions to implement the techniques introduced here may be stored on a non-transitory computer-readable storage medium and may be executed by one or more general-purpose or special-purpose programmable microprocessors. A "computer-readable storage medium", as the term is used herein, includes any mechanism that provides (i.e., stores and/or transmits) information in a form accessible by a machine (e.g., a computer, network device, personal digital assistant (PDA), mobile device, manufacturing tool, any device with a set of one or more processors, etc.). A computer-readable storage medium may include recordable/non recordable media (e.g., read-only memory (ROM), random access memory (RAM), magnetic disk or optical storage media, flash memory devices, etc.)

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

I claim:

1. A method to augment medical scan information associated with a target object on a first extended reality image, comprising:
   obtaining a three-dimensional image associated with the target object;
   identifying a first set of three-dimensional feature points from the three-dimensional image;
   identifying anatomical points based on the first set of three-dimensional feature points;
   obtaining the first extended reality image associated with the anatomical points;
   selecting a second set of three-dimensional feature points from the first extended reality image;
   performing a first image matching between the first set of three-dimensional feature points and the second set of three-dimensional feature points; and
   superimposing the three-dimensional image on the first extended reality image based on the first image matching;
   constructing a three-dimensional model based on the medical scan information;
   selecting a third set of feature points from the three-dimensional model;
   performing a second image matching between the first set of three-dimensional feature points and the third set of three-dimensional feature points to identify a matched surface associated with the three-dimensional image and the three-dimensional model;
   matching the three-dimensional model to the matched surface;
   obtaining a second extended reality image based on the matched three-dimensional model;
   superimposing the second extended reality image on the first extended reality image based on the matched surface to augment the medical scan information associated with the target object;
   obtaining a third extended reality image corresponding to an under-surface area of one or more tissues, one or more organs or one or more organ systems of a patient, wherein the third extended reality image is an image associated with the under-surface area to simulate a field of view when a surgical tool reaches the under-surface area;
   obtaining another three-dimensional image associated with the under-surface area in response to the surgical tool physically reaches the under-surface area; and
   calculating a deviation between the third extended reality image and the another three-dimensional image, wherein the deviation corresponds to a shift of the one or more tissues, one or more organs or one or more organ systems of the patient.

2. The method of claim 1, wherein the identifying anatomical points further includes marking the first set of three-dimensional feature points on the three-dimensional image.

3. The method of claim 1, wherein the first extended reality image includes one or more tissues, one or more organs or one or more organ systems of a patient including the anatomical points.

4. The method of claim 1, wherein the matching the three-dimensional model further includes rotating or shifting the three-dimensional model to match a surface defined by a plurality of points of the three-dimensional model to the matched surface.

5. The method of claim 1, wherein the matched surface is associated with a surface of one or more tissues, one or more organs or one or more organ systems of a patient.

6. The method of claim 1, further comprising obtaining a fourth extended reality image corresponding to the under-surface area based on the third extended reality image and the deviation.

7. A system, comprising:
one or more processors;
a wearable coupled to the processor; and
a non-transitory computer-readable medium having instructions stored thereon, which in response to execution by the one or more processors, cause the one or more processors to perform a method of augmenting medical scan information associated with a target object on a first extended reality image, the method comprising:
obtaining a three-dimensional image associated with the target object;
identifying a first set of three-dimensional feature points from the three-dimensional image;
identifying anatomical points based on the first set of three-dimensional feature points;
obtaining the first extended reality image associated with the anatomical points;
selecting a second set of three-dimensional feature points from the first extended reality image;
performing a first image matching between the first set of three-dimensional feature points and the second set of three-dimensional feature points; and
superimposing the three-dimensional image on the first extended reality image based on the first image matching;
wherein the non-transitory computer-readable medium having additional instructions stored thereon, which in response to execution by the one or more processors, cause the one or more processors to:
construct a three-dimensional model based on the medical scan information;
select a third set of feature points from the three-dimensional model;
perform a second image matching between the first set of three-dimensional feature points and the third set of three-dimensional feature points to identify a matched surface associated with the three-dimensional image and the three-dimensional model;
match the three-dimensional model to the matched surface;
obtain a second extended reality image based on the matched three-dimensional model;
obtain a third extended reality image corresponding to an under-surface area of one or more tissues, one or more organs or one or more organ systems of a patient, wherein the third extended reality image is an image associated with the under-surface area to simulate a field of view when a surgical tool reaches the under-surface area;
obtain another three-dimensional image associated with the under-surface area in response to the surgical tool physically reaches the under-surface area; and
calculate a deviation between the third extended reality image and the another three-dimensional image, wherein the deviation corresponds to a shift of the one or more tissues, one or more organs or one or more organ systems of the patient.

8. The system of claim 7, wherein the wearable is configured to display one or more of the first extended reality image, the second extended reality image, the third extended reality image and the fourth extended reality image.

9. The system of claim 7, wherein the non-transitory computer-readable medium having additional instructions stored thereon, which in response to execution by the one or more processors, cause the one or more processors to mark the first set of three-dimensional feature points on the three-dimensional image.

10. The system of claim 7, wherein the non-transitory computer-readable medium having additional instructions stored thereon, which in response to execution by the one or more processors, cause the one or more processors to rotate or shift the three-dimensional model to match a surface defined by a plurality of points of the three-dimensional model to the matched surface.

11. The system of claim 7, wherein the non-transitory computer-readable medium having additional instructions stored thereon, which in response to execution by the one or more processors, cause the one or more processors to superimpose the second extended reality image on the first extended reality image based on the matched surface to augment the medical scan information associated with the target object.

12. The system of claim 7, wherein the non-transitory computer-readable medium having additional instructions stored thereon, which in response to execution by the one or more processors, cause the one or more processors to obtain a fourth extended reality image corresponding to the under-surface area based on the third extended reality image and the deviation.

* * * * *